United States Patent
Mitsuya

(10) Patent No.: US 9,128,297 B2
(45) Date of Patent: Sep. 8, 2015

(54) ENDOSCOPE

(75) Inventor: Tae Mitsuya, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 1673 days.

(21) Appl. No.: 11/906,567

(22) Filed: Oct. 3, 2007

(65) Prior Publication Data

US 2008/0086031 A1   Apr. 10, 2008

(30) Foreign Application Priority Data

Oct. 5, 2006   (JP) .................................. 2006-274445

(51) Int. Cl.
| | |
|---|---|
| *A61B 1/00* | (2006.01) |
| *A61M 25/00* | (2006.01) |
| *G02B 23/24* | (2006.01) |
| *A61B 1/005* | (2006.01) |

(52) U.S. Cl.
CPC .......... *G02B 23/2476* (2013.01); *A61B 1/0052* (2013.01)

(58) Field of Classification Search
USPC .................... 600/139–152; 604/95.01–95.05, 604/523–528; 606/1; 356/241.1–241.6
See application file for complete search history.

(56) References Cited

U.S. PATENT DOCUMENTS

| | | | | |
|---|---|---|---|---|
| 4,787,369 A | * | 11/1988 | Allred et al. ................... | 600/149 |
| 5,025,804 A | * | 6/1991 | Kondo .......................... | 600/146 |
| 5,512,035 A | * | 4/1996 | Konstorum et al. .......... | 600/146 |
| 2007/0232858 A1 | * | 10/2007 | Macnamara et al. ......... | 600/149 |

FOREIGN PATENT DOCUMENTS

| | | |
|---|---|---|
| JP | 10-234654 | 9/1998 |
| JP | 2000-342516 | 12/2000 |
| JP | 2002-236260 | 8/2002 |
| JP | 2004-298446 | 10/2004 |

\* cited by examiner

*Primary Examiner* — Ryan Henderson
(74) *Attorney, Agent, or Firm* — Scully, Scott, Murphy & Presser, PC

(57) ABSTRACT

An endoscope including a bending portion in an insertion portion comprises multiple pulling members, an operation device, a driving force transfer mechanism and a biasing mechanism. The multiple pulling members are mounted on the bending portion. The operation device generates a driving force for pulling the pulling members in conjunction with a turning operation. The bending portion is bent by the operation device between an approximately straight state and a bending state. The driving force transfer mechanism transfers the driving force generated in conjunction with the turning operation of the operation device to the pulling members. The biasing mechanism provides the driving force transfer mechanism with a biasing force for turning the operation device in a reverse direction to the turning operation direction in a state where the bending portion is bent by turning the operation device.

15 Claims, 11 Drawing Sheets

ENDOSCOPE

CROSS REFERENCE TO RELATED APPLICATION

This Application claims benefit of Japanese Application No. 2006-274445 filed in Japan on Oct. 5, 2006, the contents of which are incorporated by this reference.

BACKGROUND OF THE INVENTION

1. Field of the Invention

The present invention relates to an endoscope wherein a bending portion provided to an insertion portion is bent by operating a bending operation knob provided to an operation portion.

2. Description of the Related Art

Conventionally, there has been wide use of an endoscope apparatus wherein an elongated endoscope is inserted into a body cavity or the like to allow observation and various treatments of an area to be examined to be performed. In general, an endoscope of which insertion portion is flexible has a bending portion configured by articulating multiple bending pieces provided to the insertion portion. The bending portion is configured to bend in a desired direction by operating operation means. To be more precise, the bending portion is bent at a target angle by turning a bending operation knob provided to an operation portion and thereby moving forward and backward a bending wire fixed on a distal-most bending piece constituting the bending portion. It is thereby possible to perform observation and insertion into the area to be examined with an observation optical system provided at the distal end portion of the insertion portion in a target direction.

For instance, Japanese Patent Laid-Open No. 10-234654 indicates an endoscope which has a small number of parts, is easily adjustable as to assembly and a bending angle and includes an operation portion which securely controls bending exceeding a maximum bending angle. As for the endoscope, a horizontal knob or a vertical knob is turned in a desired direction upon completing connections of connected fixing portions in all the directions, so that a horizontal sprocket or a vertical sprocket corresponding to the operations of the knobs are turned and the corresponding connected fixing portion and bending operation wire are pulled into a user side. In that case, a compressive force generated in the insertion portion is received by an insertion side guide-coil and a user side guide-coil in each direction. Therefore, a pulling force of the corresponding bending operation wire transmits to the bending portion without shrinking the insertion portion so that the bending portion bends in the desired direction.

And when fingers manipulating the knob of the endoscope are released to put the knob in a so-called free state with the bending portion bending in the desired direction as mentioned above, the bending portion in a bending state changed to return from the bending state to a straight state. It was because a bending reaction of built-in components of the endoscope was larger than a sum of an actuating force amount of the operation portion, resistance of the bending portion and a frictional force between the wire and the guide-coils.

In the case of reducing a diameter of the endoscope insertion portion in an endoscope structure of Japanese Patent Laid-Open No. 10-234654, however, the diameters of the built-in components of the endoscope are also reduced so that the bending reaction generated from the built-in components becomes smaller when the built-in components are bent as the bending portion of the endoscope bends. Thus, the bending reaction of the built-in components of the endoscope becomes smaller than the sum of the actuating force amount of the operation portion, the resistance of the bending portion and the frictional force between the wire and the guide-coils. In that case, there is a possibility that, when the knob is put in the free state, the bending state of the bending portion which has been bent may be held as-is without returning to the straight state.

In the case of the endoscope of which maximum bending angle of the bending portion is 210 degrees, the sum of the actuating force amount of the operation portion, the resistance of the bending portion and the frictional force between the wire and the guide-coils becomes very large when in the bending state of bending the bending portion at more than 180 degrees. For that reason, there is a higher possibility that, when the knob is put in the free state, the bending state of the bending portion which has been bent exceeding 180 degrees may be held as-is. In the case where the bending state of the bending portion has been held in the state of bending exceeding 180 degrees, it becomes difficult, even if the knob is in the free state, to return the bending state of the bending portion to an approximately straight state with an external force when removing the insertion portion.

For the purpose of solving the problem, Japanese Patent Laid-Open No. 2002-236260 indicates an endoscope which can naturally return the bending portion to the approximately straight state and improve operability just by putting the operation means in the free state. In the case of the endoscope, bending resistance force as a resultant force of the actuating resistance of the operation knob, the bending resistance of the bending portion alone and the frictional force between a pulling wire and external members is smaller than the sum of the bending reaction generated by the built-in components when bending the bending portion.

SUMMARY OF THE INVENTION

An endoscope including a bending portion in an insertion portion comprises multiple pulling members, operation means, a driving force transfer mechanism and a biasing mechanism. The multiple pulling members are mounted on the bending portion. The operation means generates a driving force for pulling the pulling members in conjunction with a turning operation and bends the bending portion between an approximately straight state and a bending state. The driving force transfer mechanism transfers the driving force generated in conjunction with the turning operation of the operation means to the pulling members. The biasing mechanism provides the driving force transfer mechanism with a biasing force for turning the operation means in a reverse direction to the turning operation direction in a state where the bending portion is bent by turning the operation means.

The above and other objects, features and advantages of the invention will become more clearly understood from the following description referring to the accompanying drawings.

DETAILED DESCRIPTION OF THE PREFERRED EMBODIMENTS

Hereafter, embodiments of the present invention will be described with reference to the drawings.

Hereafter, the embodiments of the present invention will be described based on the drawings.

The embodiments of an endoscope will be described with reference to FIGS. 1 to 7.

Figure 1:
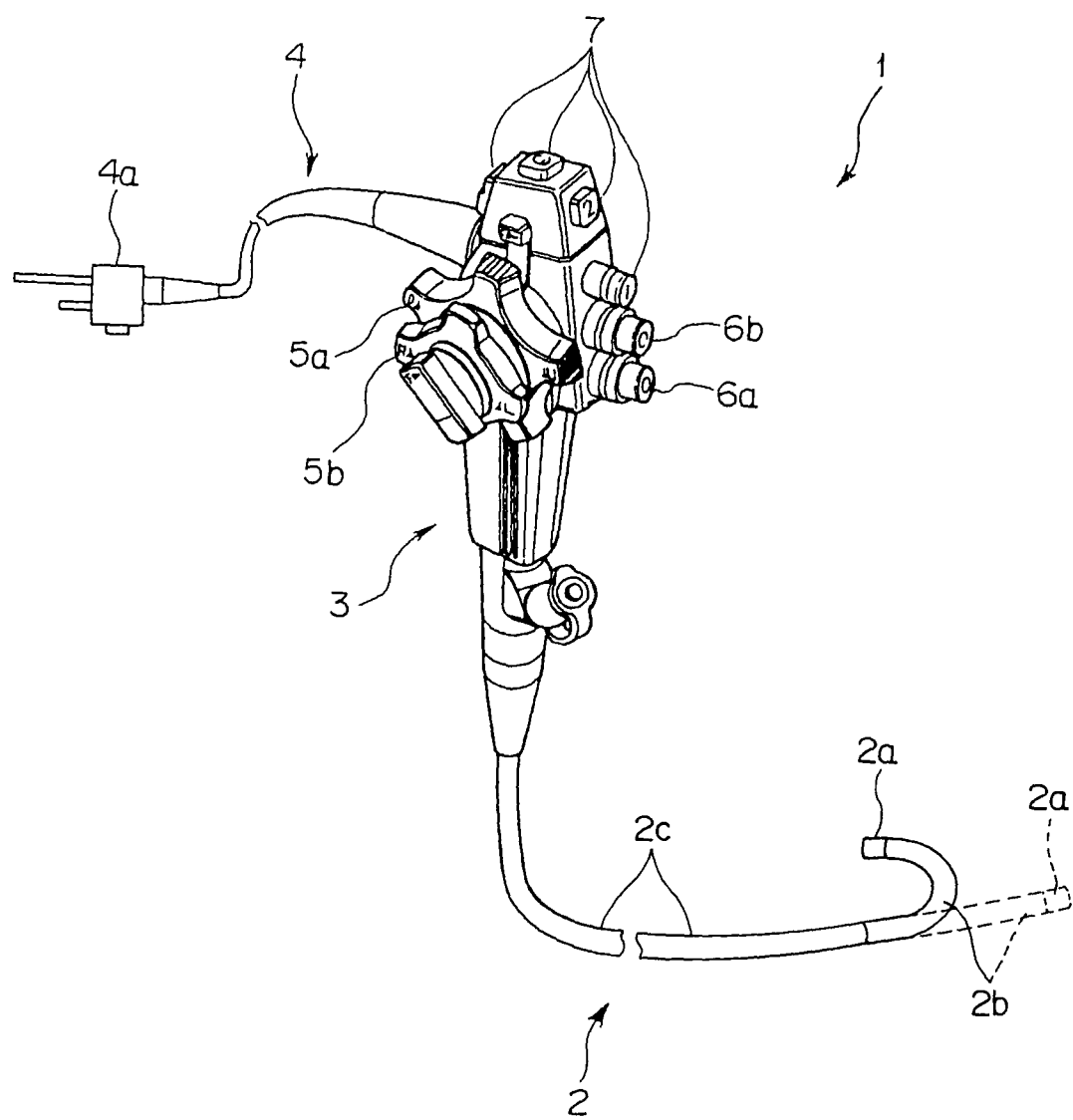
FIG. 1 is a perspective view for describing a skeleton framework of an endoscope.

As shown in FIG. 1, an endoscope 1 includes an elongated insertion portion 2 to be inserted into a body cavity through a nasal cavity or a mouth cavity for instance. The insertion portion 2 is provided, at its proximal end portion, with an operation portion 3 doubling as a grasping portion grasped by a user when used. A universal cord 4 is extended out of a side of the operation portion 3, and an endoscope connector 4a is placed at an end thereof. The universal cord 4 has a signal cable, a light guide fiber and the like which are not shown inserted therein.

The insertion portion 2 is configured by continuously placing a rigid end 2a, a bending portion 2b and a flexible tube portion 2c in order from the distal end side. The bending portion 2b is configured to be vertically and horizontally bendable by articulating multiple bending pieces.

The operation portion 3 is provided with a vertical knob 5a, a horizontal knob 5b, an air and water supply operation button 6a, a suctioning operation button 6b, various control switches 7 for controlling external devices not shown and the like as operation means. The vertical knob 5a is a bending operation knob to be grasped and turned by the user when bending the bending portion 2b in a vertical direction. The horizontal knob 5b is a bending operation knob to be grasped and turned by the user when bending the bending portion 2b in a horizontal direction.

If the vertical knob 5a is turned upward for instance by the user when the bending portion 2b of the endoscope 1 is approximately linear as indicated by a broken line in FIG. 1, the bending portion 2b changes to a bending state as indicated in full line in FIG. 1.

Figure 2:
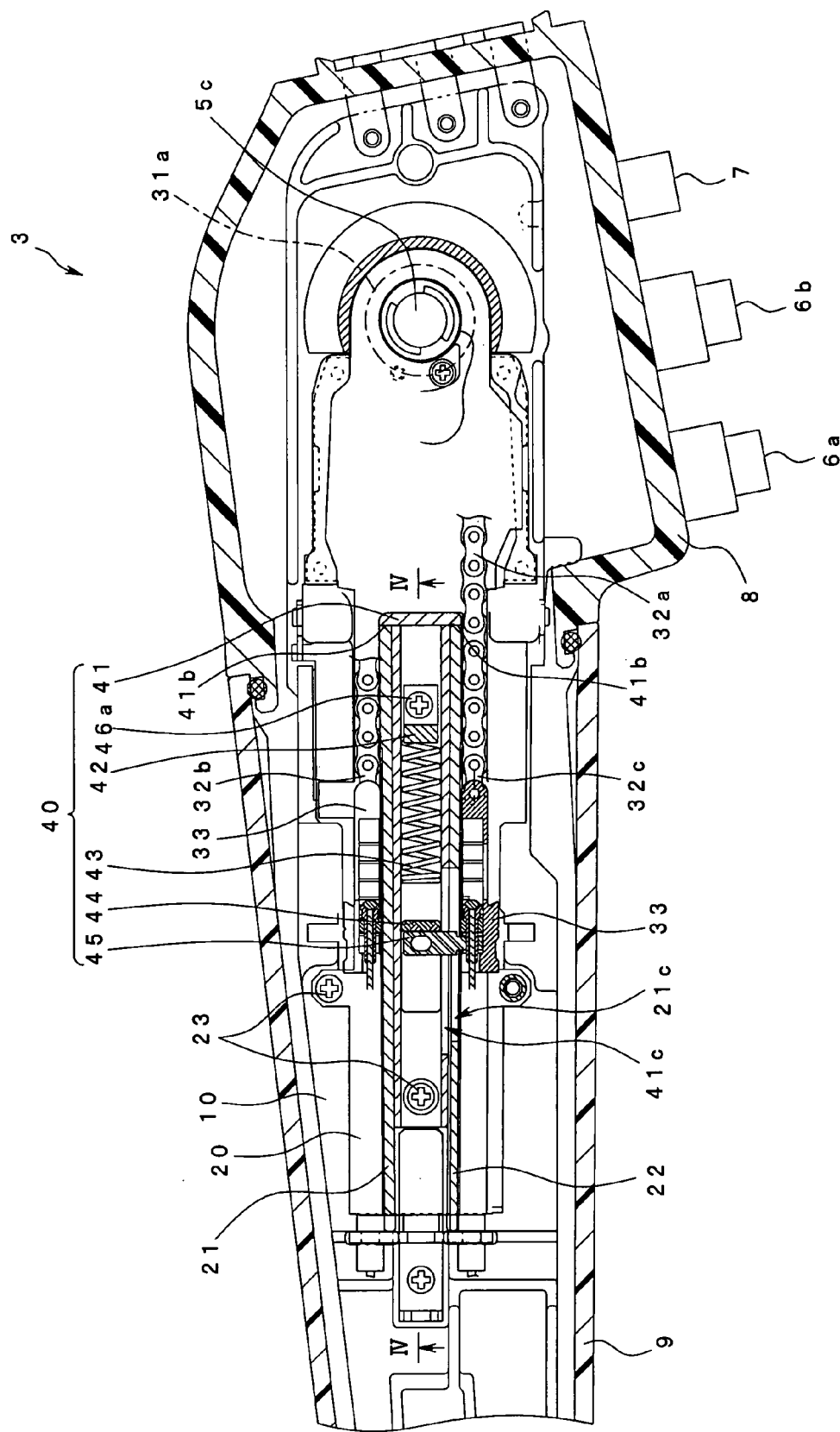
FIG. 2 is a diagram for describing a relation among a bending operation wire, a driving force transfer mechanism and a biasing mechanism provided inside an operation portion.

As shown in FIG. 2, the operation portion 3 is composed of an operation portion casing 8 and a grasping portion casing 9. The grasping portion casing 9 is watertightly connected to the distal end side of the operation portion casing 8.

A fixed plate 10 is integrally and fixedly provided inside the operation portion 3 composed of the operation portion casing 8 and the grasping portion casing 9. The fixed plate 10 is an aluminum plate for instance, and is formed by die-casting.

Through-holes not shown are formed in positions corresponding to the vertical knob 5a and the horizontal knob 5b on the fixed plate 10. A partition member 20 is threadably mounted and fixed with screw members 23 in a prescribed position on the fixed plate 10. The partition member 20 has a pair of partitions 21 and 22 erectly provided therewith.

The fixed plate 10 corresponding to the through-holes has a horizontal sprocket 31b not shown and a vertical sprocket 31a indicated by the broken line in FIG. 2 placed thereon in order from the downside. The vertical sprocket 31a is a mechanism for transferring a driving force for bending the bending portion 2b upward or downward. The vertical sprocket 31a is configured so that it is integrally fixed with an axis portion 5c of the vertical knob 5a and turns in conjunction with a turning operation of the vertical knob 5a.

The horizontal sprocket 31b is a mechanism for transferring the driving force for bending the bending portion 2b rightward or leftward. The horizontal sprocket 31b is configured so that it is integrally fixed with the axis portion (not shown) of the horizontal knob 5b and turns in conjunction with the turning operation of the horizontal knob 5b.

The vertical sprocket 31a has a vertical chain 32a constituting a driving force transfer mechanism for the vertical direction (hereafter, abbreviated as a vertical driving force transfer mechanism) wound around it. An end 32b of the vertical chain 32a is placed in an outer portion of the partition 21. The end 32b is connected with the proximal end portion of a downward bending operation wire (hereafter, abbreviated as a downward wire) 34D which is a pulling member via a connection member 33.

Figure 3:
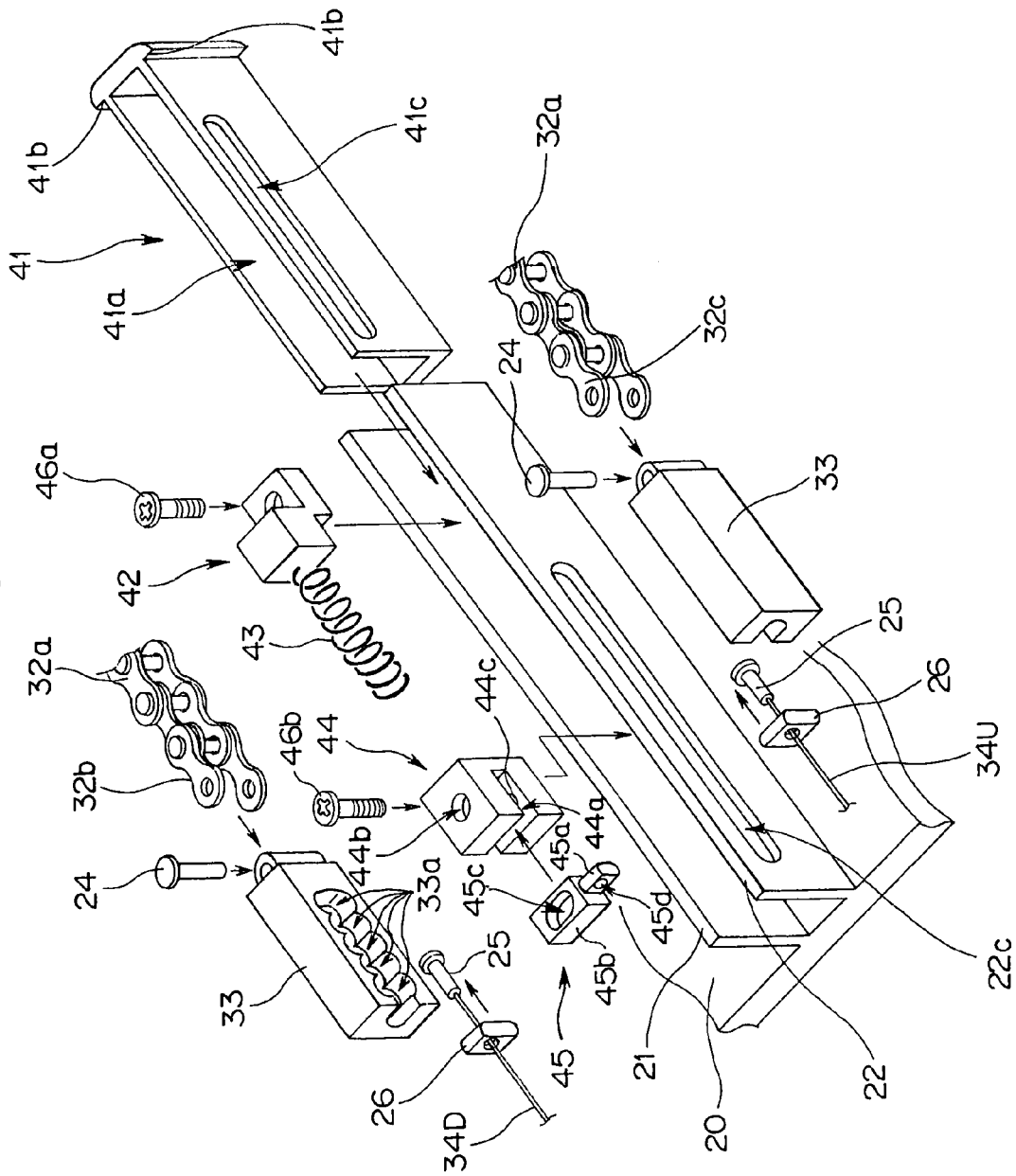
FIG. 3 is an exploded perspective view for describing configuration of the bending operation wire, the driving force transfer mechanism and the biasing mechanism.

To be more precise, as shown in FIG. 3, the end 32b of the vertical chain 32a is connected with the connection member 33 by a coupling pin 24. The connection member 33 is connected with the proximal end portion of the downward wire 34D by engagingly placing a positioning member 26 placed in a wire end configuration portion 25 in multiple mounting holes 33a provided on the connection member 33. The wire end configuration portion 25 is provided to the proximal end portion of the downward wire 34D. The mounting holes 33a are the holes provided on the connection member 33 at a prescribed pitch. The multiple mounting holes 33a are intended to eliminate slackness of the wire when the wire has been extended, where the slackness is eliminated by displacing the position of the mounting hole 33a in which the positioning member 26 is placed.

The other end 32c of the vertical chain 32a is placed on the outer portion of the partition 22. The other end 32c is connected with the proximal end portion of an upward bending operation wire (hereafter, abbreviated as an upward wire) 34U via the connection member 33.

To be more precise, as shown in FIG. 3, the other end 32c of the vertical chain 32a is connected with the connection member 33 by the coupling pin 24. The connection member 33 is connected with the proximal end portion of the upward wire 34U by placing the positioning member 26 placed in the wire end configuration portion 25 in the multiple mounting holes 33a not shown provided on the connection member 33. The wire end configuration portion 25 is provided to the proximal end portion of the upward wire 34U.

The end of the upward wire 34U and the end of the downward wire 34D are fixedly placed in prescribed positions on distal end bending pieces not shown constituting the bending portion 2b respectively.

Therefore, if the user turns the vertical knob 5a to bend the bending portion 2b upward, the vertical sprocket 31a is turned first, and the vertical chain 32a moves in conjunction with the turning of the vertical sprocket 31a. The connection member 33 moves in conjunction with the movement of the vertical chain 32a. The upward wire 34U is pulled in conjunction with the movement of the connection member 33.

Then, a pulling force thereof is transferred to the bending portion 2b so that the bending portion 2b bends upward. In other words, the bending portion 2b changes its bending state to upward as the driving force generated in conjunction with the turning operation of the vertical knob 5a is transferred to the upward wire 34U via the vertical sprocket 31a, the vertical chain 32a and the connection member 33. On the other hand, the bending portion 2b changes its bending state to downward as the driving force generated in conjunction with the turning operation of the vertical knob 5a is transferred to the downward wire 34D via the vertical sprocket 31a, the vertical chain 32a and the connection member 33.

The upward wire 34U is placed approximately in parallel with the partition 22, and the downward wire 34D is placed approximately in parallel with the partition 21. To be more specific, the upward wire 34U and the downward wire 34D are placed approximately in parallel.

According to the present embodiment, a driving force transfer mechanism for the horizontal direction (hereafter, abbreviated as a horizontal driving force transfer mechanism) including the horizontal sprocket 31b is placed on the downside of the vertical driving force transfer mechanism mentioned above. Therefore, it is not shown.

However, the horizontal sprocket 31b has a horizontal chain 32d constituting the horizontal driving force transfer mechanism wound around it. An end of the horizontal chain 32d is placed in an outer portion of the partition 21. The end of the horizontal chain 32d is connected with the proximal end portion of a leftward wire 34L via the connection member 33 constituting the horizontal driving force transfer mechanism.

The other end of the horizontal chain 32d is placed in the outer portion of the partition 22. The other end of the horizontal chain 32d is connected with the proximal end portion of a rightward wire 34R via the connection member 33 constituting the horizontal driving force transfer mechanism. A distal end portion of the leftward wire 34L is fixedly placed in the prescribed position on the distal end bending piece constituting the bending portion 2b. The distal end portion of the rightward wire 34R is fixedly placed in the prescribed position on the distal end bending piece constituting the bending portion 2b.

Therefore, the leftward wire 34L is pulled in conjunction with the turning operation of the horizontal knob 5b so that the bending portion 2b bends leftward. The rightward wire 34R is pulled in conjunction with the turning operation of the horizontal knob 5b so that the bending portion 2b bends rightward.

As shown in FIG. 2, a biasing mechanism 40 is provided between an inner portion of the partition 21 and the inner portion of the partition 22. In the state where the bending portion 2b is bent upward, the biasing mechanism 40 generates a biasing force in the direction for returning the bending state of the bending portion 2b to an approximately straight state.

The biasing mechanism 40 is configured by including a sliding platform 41, a fixing member 42, a helical compression spring 43 which is a push spring, a sliding member 44 and an arm portion forming member 45, and also has various set screws 46a and 46b. Within a space portion (refer to reference character 41a) described later of the sliding platform 41, there are the fixing member 42, the helical compression spring 43 and the sliding member 44 placed in order from the axis portion 5c side along a longitudinal axis direction.

Moreover, the approximately straight state refers to the bending state of the bending portion in the state where no pulling force is acting on the bending operation wires 34U, 34D, 34L and 34R which are pulled when putting the bending portion 2b in the bending state.

As shown in FIG. 3, the sliding platform 41 constituting the biasing mechanism 40 is an elongated rectangular parallelepiped-shaped member, which is placed in the space portion formed between the partition 21 and the partition 22. The sliding platform 41 includes a space portion 41a which has open ends on a top face and one short side in FIG. 3. The fixing member 42, the helical compression spring 43 and the sliding member 44 are placed in the prescribed positions of the space portion 41a. Reference character 41b denotes a positioning portion. The positioning portion 41b is formed by projecting by a prescribed amount, and is placed to contact a proximal end face of each of the partition 21 and the partition 22. Reference character 41c denotes a long hole. The long hole 41c is formed along the longitudinal axis in prescribed length and dimensions in a prescribed position on one longitudinal side face of the sliding platform 41 placed on the partition 22 side. The long hole 41c is provided with an arm portion 45a described later which is mounted on the arm portion forming member 45. The partition 22 has an elongated long hole 22c along the longitudinal axis formed thereon correspondingly to the long hole 41c.

Figure 4:
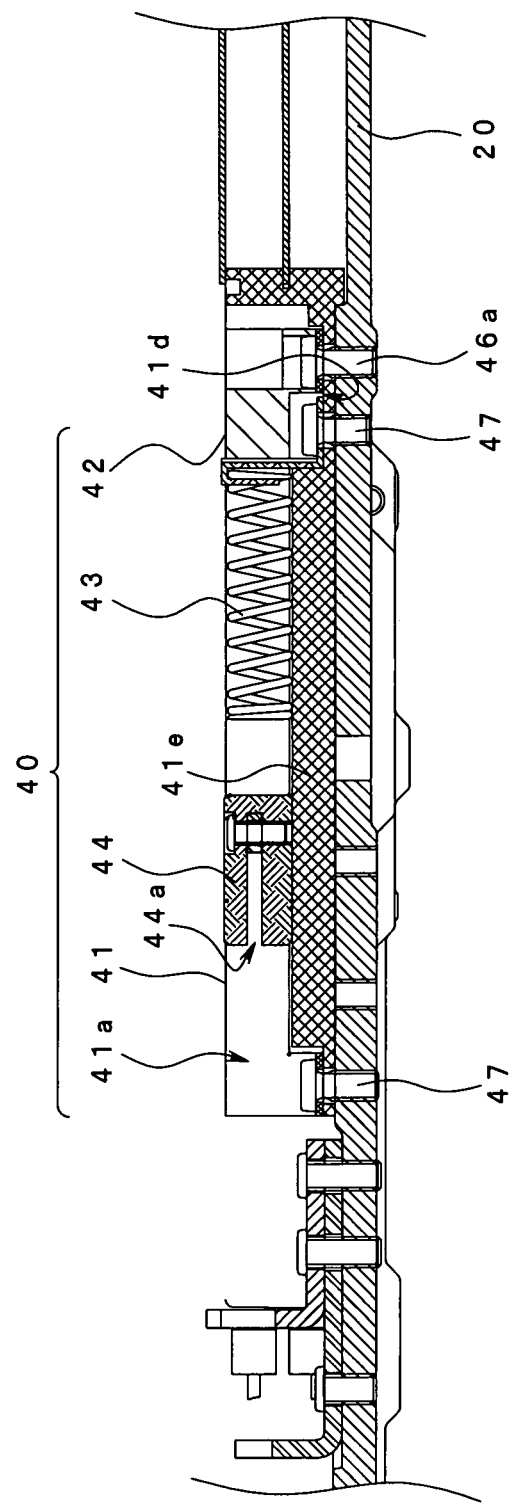
FIG. 4 is an IV to IV line sectional view of FIG. 2.

As shown in FIGS. 2 and 4, the sliding platform 41 is integrally fixed on the fixed plate 10 by a fixing screw 47 with the positioning portion 41b contacting the end face of each of the partitions 21 and 22. A convex portion 41e formed higher than a bottom face 41d by a prescribed dimension is provided in the space portion 41a of the sliding platform 41. On the top face of the convex portion 41e, the sliding member 44 is slidably placed and the helical compression spring 43 is mounted.

The fixing member 42 constituting the biasing mechanism 40 has one end side of the helical compression spring 43 integrally placed thereon. The fixing member 42 having one end side of the helical compression spring 43 integrally placed thereon is integrally fixed on the fixed plate 10 by the set screw 46a. The helical compression spring 43 is thereby integrally fixed to the operation portion 3. An escape hole for inserting the set screw 46a for fixing the fixing member 42 is formed on the bottom face 41d of the sliding platform 41.

The sliding member 44 constituting the biasing mechanism 40 includes a notch groove 44a. The notch groove 44a has a body portion 45b constituting the arm portion forming member 45 loosely placed therein. A counterbore 44b where a head of the set screw 46b is placed is provided in a rectangular parallelepiped portion by sandwiching the notch groove 44a on the upside in the drawings. A female screw 44c with which a screw portion of the set screw 46b is screwed together is formed in the rectangular parallelepiped portion by sandwiching the notch groove 44a on the downside in the drawings.

The arm portion forming member 45 constituting the biasing mechanism 40 is configured by including the arm portion 45a and the body portion 45b. The body portion 45b has an escape hole 45c in which the set screw 46b is inserted and placed formed thereon. The arm portion 45a is configured in the shape and length placeable in the mounting holes 33a. Reference character 45d denotes a wire escape concave portion. The wire escape concave portion 45d has the upward wire 34U inserted and placed therein.

The arm portion forming member 45 is loosely fixed on the sliding member 44. To be more precise, the arm portion forming member 45 is loosely fixed by screwing the screw portion of the set screw 46b together with the female screw 44c via the escape hole 45c with the arm portion forming member 45 placed in the notch groove 44a of the sliding member 44. To be more specific, the arm portion forming member 45 is put in an integrated state with the sliding member 44 with desired wobbling.

The sliding member 44 integrated with the arm portion forming member 45 is placed on the top face of the convex portion 41e. In the placement state, the arm portion 45a provided to the arm portion forming member 45 passes through the long holes 41c and 22c and gets projected into the outer portion of the partition 22. The positioning member 26 provided on the proximal end portion of the upward wire 34 is placed on one end face side of the arm portion 45a projected from the partition 22. In the placement state, the arm portion 45a and the positioning member 26 are placed in the mounting holes 33a provided on the connection member 33.

Thus, as shown in FIG. 2, the sliding member 44 connected to the connection member 33 via the arm portion forming member 45 is slidably placed on the top face of the convex portion 41e. In the placement state, the sliding member 44 slidingly moves on the convex portion 41e in conjunction with the movement of the connection member 33.

A description will be given as to workings of the endoscope 1 including the biasing mechanism 40 configured as described above.

Figure 5:
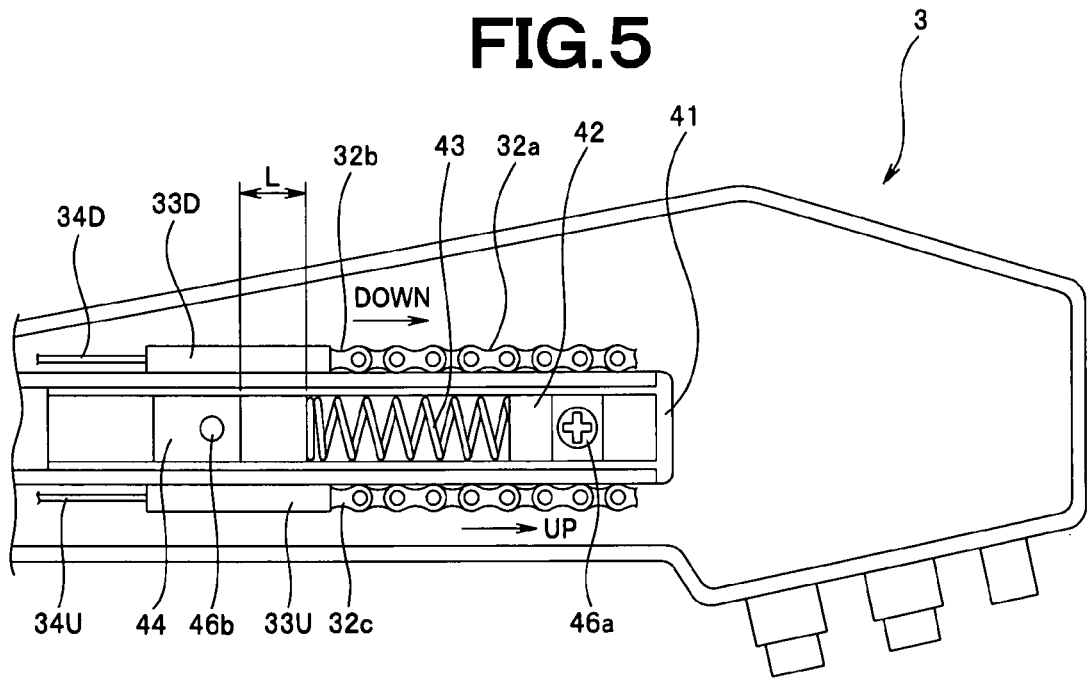
FIG. 5 is a pattern diagram for describing the biasing mechanism when a bending portion is in an approximately straight state.

When the bending portion 2b of the endoscope 1 is approximately linear as indicated by the broken line in FIG. 1, the connection member 33 connected with the downward wire 34D (hereafter, referred to as a downward connection member 33D) and the connection member 33 connected with the upward wire 34U (hereafter, referred to as an upward connection member 33U) are placed in approximately the same location in the longitudinal axis direction in the operation portion 3 as shown in FIGS. 2 and 5. As shown in FIG. 5, there is a state of separation by a distance L between one end face of the sliding member 44 and a distal end face of the helical compression spring 43 connected with the upward connection member 33U via the arm portion 45a of the arm portion forming member 45.

Here, to bend the bending portion 2b upward, the user grasps the vertical knob 5a and turns it in an upper bending direction.

Upon start of the turning operation of the vertical knob 5a, the vertical sprocket 31a is turned in the same direction. And in conjunction with the turning, the vertical chain 32a wound around the vertical sprocket 31a moves to an UP direction indicated by an arrow in FIG. 5. The upward connection member 33U moves in the same direction in conjunction with the movement of the vertical chain 32a. And the upward wire 34U connected to the upward connection member 33U via the positioning member 26 is pulled in the UP direction by the movement of the upward connection member 33U. In conjunction with the pulling of the upward wire 34U, the bending upward of the bending portion 2b is started. In conjunction with the pulling of the upward wire 34U, the sliding member 44 connected to the upward connection member 33U via the arm portion forming member 45 starts moving toward the distal end face of the helical compression spring 43.

As the user continues to turn the vertical knob 5a, the vertical chain 32a further moves in the UP direction. The upward connection member 33U moves in the same direction in conjunction with the further movement of the vertical chain 32a. And the upward wire 34U is further pulled in the UP direction by the further movement of the upward connection member 33U so that the bending state changes to increase an upward bending angle of the bending portion 2b. The one end face of the sliding member 44 moving in conjunction with the movement of the upward connection member 33U contacts the distal end face of the helical compression spring 43.

In the contact state, the sum of the actuating force amount of the vertical knob 5a, the resistance of the bending portion 2b and the frictional force between the wires 34D, 34U and the guide-coils not shown is smaller than the bending reaction of the built-in components of the endoscope. Therefore, when the user releases the fingers from the vertical knob 5a to put the vertical knob 5a in the free state, the bending portion 2b in the bending state returns to the approximately straight state.

Figure 6:
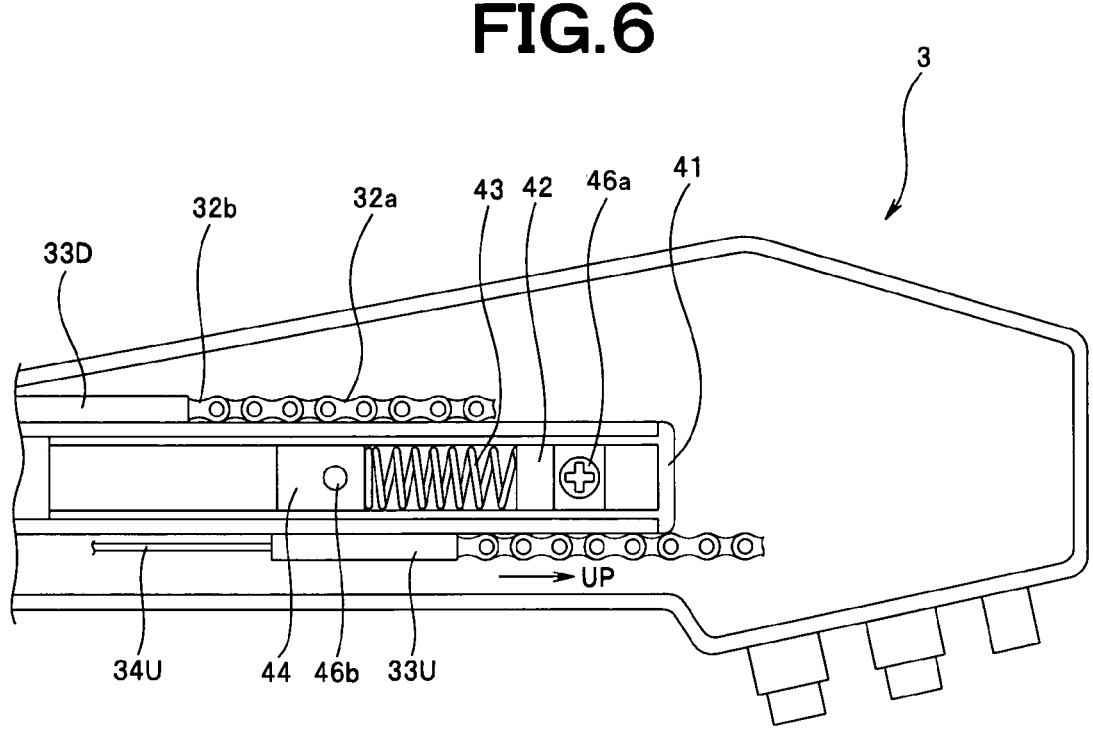
FIG. 6 is a pattern diagram for describing the biasing mechanism when the bending portion is bent upward.

Thereafter, if the user further turns the vertical knob 5a in the UP direction, the upward connection member 33U is moved in the UP direction in conjunction with the turning operation. And the bending angle of the bending portion 2b becomes even larger so as to be in the bending state where the bending angle is bending at 180 degrees or more as shown in full line in FIG. 1 for instance. As the upward connection member 33U moves, the sliding member 44 having been in contact with the distal end face of the helical compression spring 43 moves while pressurizing the distal end face side of the helical compression spring 43 so as to be in the state of compressing the helical compression spring 43 as shown in FIG. 6.

In the bending state, the sum of the actuating force amount of the vertical knob 5a, the resistance of the bending portion 2b and the frictional force between the wires 34D, 34U and the guide-coils not shown becomes larger than the bending reaction of the built-in components of the endoscope. For that reason, as to a conventional endoscope, there have been the cases where, when the user releases the fingers grasping the vertical knob 5a in the bending state to put the vertical knob 5a in the free state, the bending state of the bending portion 2b is maintained as-is. According to the present embodiment, however, the helical compression spring 43 is compressed in the bending state. Therefore, when the user releases the fingers from the vertical knob 5a to put the vertical knob 5a in the free state, the sliding member 44 is moved in a reverse direction to the UP direction by receiving an extrusion force amount which is the biasing force of the helical compression spring 43.

And in conjunction with the movement of the sliding member 44, the upward connection member 33U connected with the sliding member 44 via the arm portion forming member 45 is moved in the reverse direction to the UP direction, that is, a DOWN direction. And in conjunction with the movement of the upward connection member 33U in the DOWN direction, the vertical chain 32a connected to the upward connection member 33U is also moved in the DOWN direction.

Thus, the vertical sprocket 31a having the vertical chain 32a wound around it is turned in a downward bending direction which is the reverse direction to an upward bending direction so that the vertical knob 5a is put in the state of being turned in the downward bending direction. As the vertical knob 5a is put in the state of being turned in the downward bending direction, the bending portion 2b having the bending angle of 180 degrees changes to be in the approximately straight state as shown in solid line in FIG. 1.

To be more specific, when the user releases the fingers from the vertical knob 5a in the state where the bending angle of the bending portion 2b is bending upward at 180 degrees or more, the sliding member 44 is moved by the extrusion force of the helical compression spring 43 which has been compressed. And in conjunction with the movement of the sliding member 44, the connection member 33 and the vertical chain 32a connected to the sliding member 44 via the arm portion forming member 45 are moved in the DOWN direction so that the bending portion 2b in the bending state changes to the approximately straight state.

Thus, the biasing mechanism includes a coil spring and the sliding member placed opposite the coil spring to be moved in conjunction with the movement of the connection member. The biasing mechanism has a configuration wherein, when the connection member is moved for bending in a prescribed direction, the sliding member is moved toward the distal end face of the coil spring and the coil spring is compressed thereafter.

Therefore, even in the case where, in the bending state of the bending portion, the sum of the actuating force amount of the operation portion, the resistance of the bending portion and the frictional force between the wires and the guide-coils is larger than the bending reaction of the built-in components of the endoscope, it is possible, when the bending operation knob is put in the free state, to put the bending portion in the bending state in the approximately straight state by the biasing force of the coil spring without depending on the reaction of the built-in components of the endoscope.

That is because, as the position of the sliding member is moved from a bending state position toward an approximately straight state position by the biasing force of the coil spring, the connection member and the chain are moved in conjunction with the movement of the sliding member.

Thus, it is possible to improve operability since the bending portion in the bending state turns toward the approximately straight state when the fingers are released from the bending operation knob which is bending the bending portion in the bending state of the bending portion.

In the present embodiment, it is assumed that one end face of the sliding member 44 and the distal end face of the helical compression spring 43 are in the separated state by a distance L. However, an initial state may be the state where one end face of the sliding member 44 and the distal end face of the helical compression spring 43 are in contact (L=0) or in proximity.

Thus, the helical compression spring 43 changes toward a compressed state simultaneously or almost simultaneously with operating the vertical knob 5a in the upward bending direction for the sake of bending the bending portion 2b upward. In that case, the helical compression spring 43 is put in the compressed state in the state where the bending portion 2b is bent. Therefore, in the free state where the fingers of the user are released from the vertical knob 5a, the bending portion 2b in the bending state is put in the approximately straight state by the extrusion force amount which is the biasing force of the helical compression spring 43.

According to the present embodiment, the biasing mechanism is only provided to an upward driving force transfer mechanism. It is because of the configuration wherein only the upward bending angle of the bending portion 2b can be bent up to 210 degrees for instance exceeding 180 degrees. It is also intended to prevent the insertion portion from being pulled out in the bending state.

According to the present embodiment, the downward connection member 33D and the upward connection member 33U are placed in approximately the same position in the longitudinal axis direction as shown in FIG. 5, and the bending portion 2b is approximately linear as indicated by the broken line in FIG. 1. In that case, the user turns the vertical knob 5a in the downward bending direction in order to bend the bending portion 2b downward.

Figure 7:
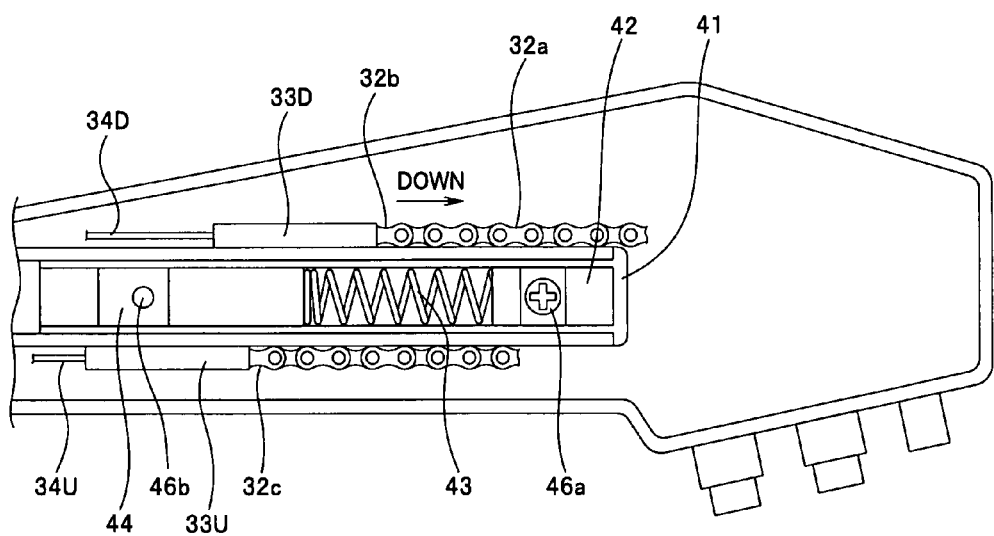
FIG. 7 is a pattern diagram for describing the biasing mechanism when the bending portion is bent downward.

In conjunction with a start of the turning operation of the vertical knob 5a, the vertical sprocket 31a is turned in the same direction. And in conjunction with the turning, the vertical chain 32a wound around the vertical sprocket 31a moves in the DOWN direction indicated by an arrow in FIG. 5. The downward connection member 33D moves in the same direction in conjunction with the movement of the vertical chain 32a. And the downward wire 34D connected to the downward connection member 33D via the positioning member 26 is pulled in the DOWN direction by the movement of the downward connection member 33D. In conjunction with the pulling of the downward wire 34D, the bending portion 2b bends downward. In that case, as shown in FIG. 7, the sliding member 44 connected to the upward connection member 33U via the arm portion forming member 45 moves in the direction for further separating from the distal end face of the helical compression spring 43.

According to the present embodiment, the coil spring is the push spring. However, the coil spring is not limited to the push spring but may be composed of a pull spring as shown in FIGS. 8 to 11.

Figure 8:
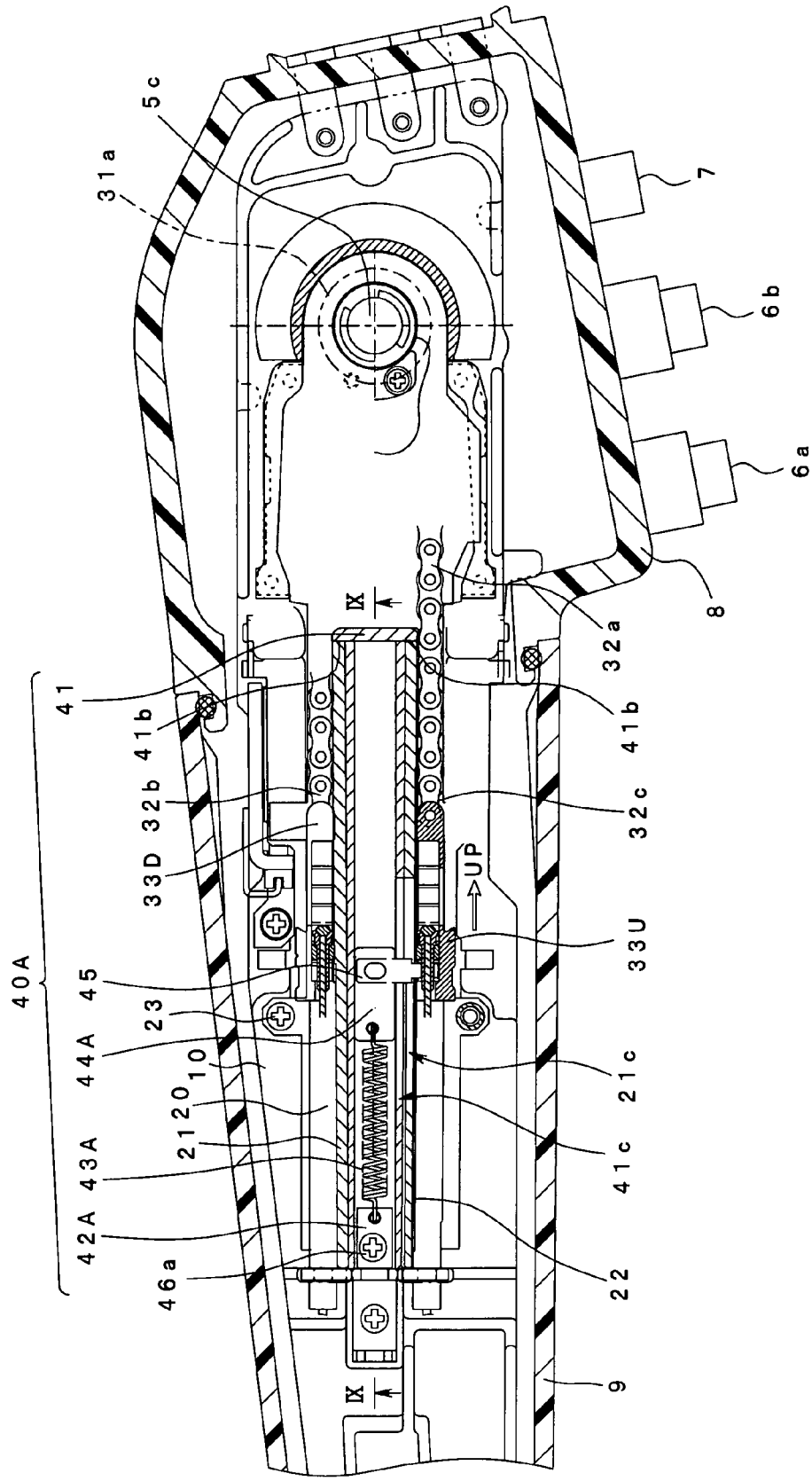
FIG. 8 is a diagram for describing a relation among the bending operation wire, the driving force transfer mechanism and the biasing mechanism having a coil spring as a pulling spring provided inside the operation portion.
Figure 9:
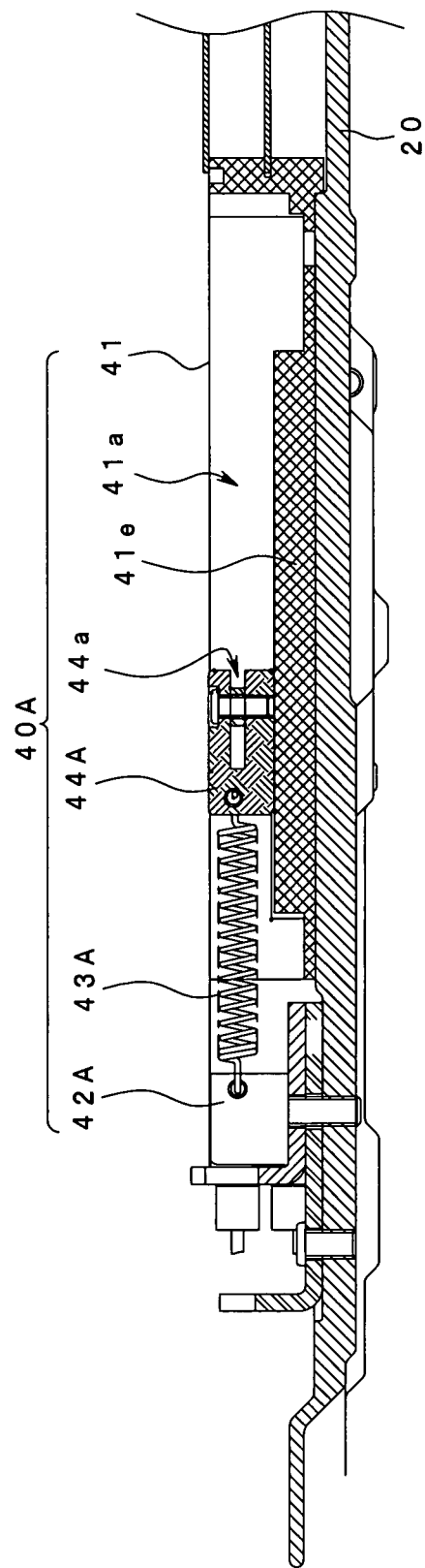
FIG. 9 is an IX to IX line sectional view of FIG. 8.

As shown in FIG. 8, the operation portion 3 of the endoscope 1 of the present embodiment includes a biasing mechanism 40A. The biasing mechanism 40A is configured by including the sliding platform 41, a fixing member 42A, a coil spring 43A which is a pull spring, a sliding member 44A and the arm portion forming member 45. Within the space portion 41a of the sliding platform 41, there are the sliding member 44A, the coil spring 43A and the fixing member 42A placed in order from the axis portion 5c side along the longitudinal axis direction.

The fixing member 42A constituting the biasing mechanism 40A can have the proximal end side of the coil spring 43A mounted thereon. The fixing member 42A is integrally fixed on the fixed plate 10 by the set screw 46a. The coil spring 43A is integrally fixed to the operation portion 3 by mounting the proximal end side of the coil spring 43A on the fixing member 42A.

The sliding member 44A constituting the biasing mechanism 40A can have the proximal end side of the coil spring 43A mounted thereon. The sliding member 44A is slidably placed on the top face of the convex portion 41e by facing a reverse direction to the above-mentioned embodiment. For that reason, the proximal end side of the coil spring 43A is mounted on the distal end face opposite to an opening of the notch groove 44a provided to the sliding member 44A. The rest of the configuration is the same as the above-mentioned embodiment, and the same members are given the same symbols and a description thereof will be omitted.

A description will be given as to workings of the endoscope 1 including the biasing mechanism 40A configured as described above.

When the bending portion 2b of the endoscope 1 is approximately linear as indicated by the broken line in FIG. 1, the downward connection member 33D and the upward connection member 33U are placed in approximately the same position in the longitudinal axis direction within the operation portion 2c as shown in FIG. 8. According to the present embodiment, the proximal end side of the coil spring 43A is mounted on the distal end face side of the sliding member 44A connected with the upward connection member 33U via the arm portion 45a of the arm portion forming member 45.

Here, to bend the bending portion 2b upward, the user grasps the vertical knob 5a and turns it in the upper bending direction. With the start of the turning operation of the vertical knob 5a, the vertical sprocket 31a is turned in the same direction. And in conjunction with the turning, the vertical chain 32a wound around the vertical sprocket 31a moves in the UP direction indicated by the arrow in FIG. 8. The upward connection member 33U moves in the same direction in conjunction with the movement of the vertical chain 32a. And the upward wire 34U connected to the upward connection member 33U via the positioning member 26 is pulled in the UP direction by the movement of the upward connection member 33U. In conjunction with the pulling of the upward wire 34U, upward bending of the bending portion 2b is started. In conjunction with the pulling of the upward wire 34U, the sliding member 44A connected to the upward connection member 33U via the arm portion forming member 45 moves while pulling the coil spring 43A.

As the user continues to turn the vertical knob 5a, the vertical chain 32a further moves in the UP direction. The upward connection member 33U also moves in the same direction in conjunction with the further movement of the vertical chain 32a. And the upward wire 34U is further pulled in the UP direction by the movement of the upward connection member 33U in the same direction so that the bending state changes to increase the upward bending angle of the bending portion 2b. The coil spring 43A is put in a further pulled state by the sliding member 44A which has been moving in conjunction with the movement of the upward connection member 33U.

According to the present embodiment, when the user releases the fingers from the vertical knob 5a with the bending portion 2b bent, that is, with the coil spring 43A pulled so as to put the vertical knob 5a in the free state, the sliding member 44A is moved in the reverse direction to the UP direction. That is because the biasing force of the coil spring 43A is the pullback force amount.

And in conjunction with the movement of the sliding member 44A in the DOWN direction, the upward connection member 33U connected with the sliding member 44A via the arm portion forming member 45 is moved in the DOWN direction. And the vertical chain 32a connected to the upward connection member 33U also moves in the DOWN direction.

Thus, as with the above-mentioned embodiment, the vertical sprocket 31a having the vertical chain 32a wound around it is turned in the downward bending direction which is the reverse direction to the upward bending direction so that the vertical knob 5a is put in the state of being turned in the downward bending direction. As the vertical knob 5a is put in the state of being turned in the downward bending direction, the bending portion 2b having been in the bending state as indicated in full line in FIG. 1 changes toward the approximately straight state.

Thus, according to the present embodiment, when the user releases the fingers from the vertical knob in the bending state where the bending portion is bent upward, it is possible to put the bending portion in the approximately straight state by the pullback force amount of the extended coil spring. That is because, in conjunction with the movement of the sliding member moved by the pullback force amount of the coil spring, the upward connection member and the vertical chain connected to the sliding member via the arm portion forming member are moved in the DOWN direction.

The other workings and effects are the same as those in the above-mentioned embodiment.

Figure 10:
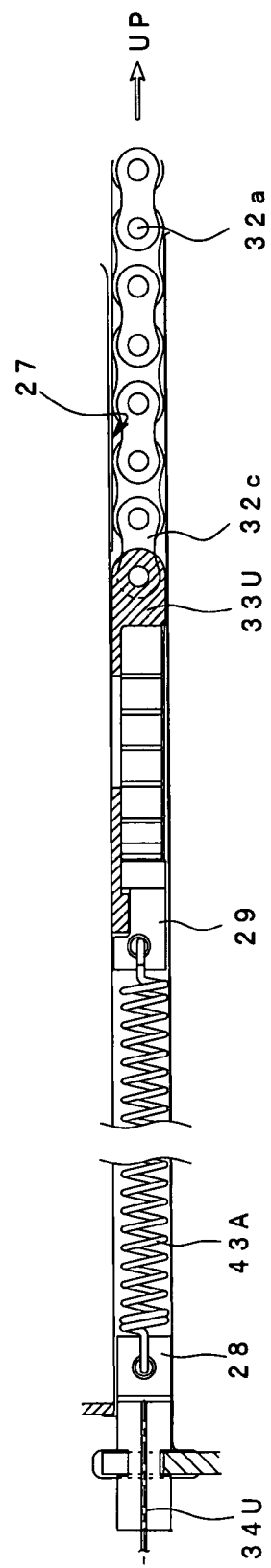
FIG. 10 is a diagram for describing a first variation of the biasing mechanism.

As shown in FIG. 10, the coil spring 43A of the pull string type is placed in an upward partition space 27 provided to the partition member 20. The distal end side of the coil spring 43A is mounted on a fixing member 28. The fixing member 28 is fixed in a prescribed position within the space 27. The proximal end side of the coil spring 43A is mounted on a wire connecting member 29 provided to the upward connection member 33U. The wire connecting member 29 has the proximal end portion of the upward wire 34U fixed thereon. The upward wire 34U is inserted into the through-hole not shown provided to fixing member 28 in the coil spring 43A so as to be extended out on the distal end side.

In the configuration, when the user turns the vertical knob 5a and the vertical chain 32a is moved in the UP direction, the upward connection member 33U is moved in conjunction with the movement of the vertical chain 32a so that the upward wire 34U is pulled in the UP direction and the bending portion 2b is bent upward. The coil spring 43A changes to the pulled state in conjunction with the movement of the upward connection member 33U.

According to the present embodiment, when the user releases the fingers from the vertical knob 5a to put the vertical knob 5a in the free state in the pulled state of the coil spring 43A, the upward connection member 33U is moved in the reverse direction to the UP direction by the pullback force amount which is the biasing force of the coil spring 43A.

And the vertical chain 32a connected to the upward connection member 33U moves in the DOWN direction. Thus, as with the above-mentioned embodiment, the vertical sprocket 31a having the vertical chain 32a wound around it is turned in the downward bending direction which is the reverse direction to the upward bending direction so that the vertical knob 5a is put in the state of being turned in the downward bending direction. As the vertical knob 5a is put in the state of being turned in the downward bending direction, the bending portion 2b having been in the bending state as indicated in full line in FIG. 1 changes toward the approximately straight state.

Thus, the coil spring of the pull string type is placed in the prescribed partition space provided in a partition portion of the partition member. Therefore, when the user releases the fingers from the bending operation knob in bending operation, the chain is moved in the reverse direction to the bending operation direction by the pullback force amount of the extended coil spring. It is thereby possible to securely put the bending portion in the approximately straight state by the biasing force of the coil spring.

And the coil spring is placed not only in the upward partition space provided in the partition portion of the partition member but also in a rightward partition space for instance. Thus, it is possible, when the bending portion is bent either in the upward bending direction or in the rightward bending direction, to securely put the bending portion in the bending state in the approximately straight state by the biasing force of the coil spring.

According to the present embodiment, the coil spring is placed in the partition space. Therefore, it is possible to make efficient use of the inside of the operation portion by eliminating the space for providing the sliding member from the partition member.

According to the above-mentioned embodiment, the bending directions of the bending portion 2b of the endoscope 1 are the four directions of up, down, left and right. Depending on the endoscope, however, there are the cases where the bending directions of the bending portion are the two directions of up and down. In that case, the configuration shown in FIG. 11 and the configuration shown in FIG. 12 are thinkable.

A second variation will be described with reference to FIG. 11.

Figure 11:
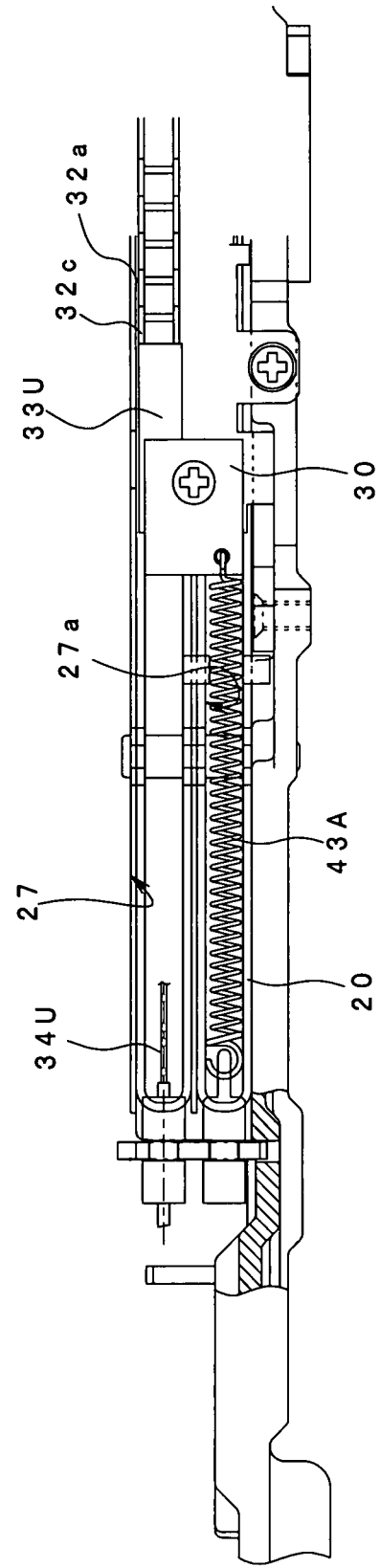
FIG. 11 is a diagram for describing a second variation of the biasing mechanism.
Figure 12:
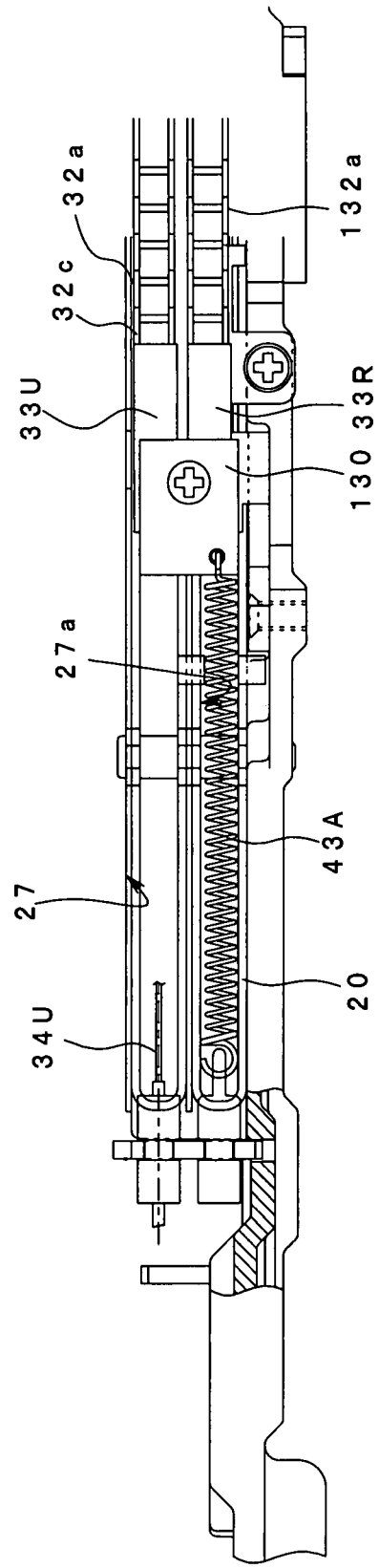
FIG. 12 is a diagram for describing a third variation of the biasing mechanism.

As shown in FIG. 11, the driving force transfer mechanism is provided in the upward partition space 27 provided to the partition member 20, and a rightward partition space 27a positioned on the downside of the upward partition space 27 becomes a free space.

In the case of the configuration above, the coil spring 43A of the pull string type is placed in the rightward partition space 27a as shown in FIG. 11. The distal end side of the coil spring 43A is mounted in the prescribed position within the rightward partition space 27a, and the proximal end side of the coil spring 43A is mounted on a spring connecting member 30 integrally fixed on the upward connection member 33U.

In the configuration, when the user turns the vertical knob 5a and the vertical chain 32a is moved in the UP direction, the upward connection member 33U is moved in conjunction with the movement of the vertical chain 32a so that the upward wire 34U is pulled in the UP direction and the bending portion 2b is bent upward. In conjunction with the movement of the upward connection member 33U, the coil spring 43A mounted on the spring connecting member 30 integral with the upward connection member 33U changes to the pulled state.

According to the present embodiment, when the user releases the fingers from the vertical knob 5a to put the vertical knob 5a in the free state in the pulled state of the coil spring 43A, the upward connection member 33U is moved in the reverse direction to the UP direction by the pullback force amount which is the biasing force of the coil spring 43A.

And the vertical chain 32a connected to the upward connection member 33U moves in the DOWN direction. Thus, as with the above-mentioned embodiment, the vertical sprocket 31a having the vertical chain 32a wound around it is turned in the downward bending direction which is the reverse direction to the upward bending direction so that the vertical knob 5a is put in the state of being turned in the downward bending direction. As the vertical knob 5a is put in the state of being turned in the downward bending direction, the bending portion 2b having been in the bending state as indicated in full line in FIG. 1 changes toward the approximately straight state.

Thus, it is possible to obtain the same workings and advantages as those of the above-mentioned embodiment.

A third variation will be described with reference to FIG. 12.

As shown in FIG. 12, the driving force transfer mechanism is provided in the upward partition space 27 provided to the partition member 20, and the rightward partition space 27a positioned on the downside of the upward partition space 27 becomes a free space. The bending in the two directions of the present embodiment does not require a horizontal chain 132a which is in the position to be used in the case of bending in the four directions. However, the horizontal chain 132a is placed so as to work in conjunction with the vertical chain 32a through the sprocket 31b not shown.

In the case of the configuration above, the coil spring 43A of the pull string type is placed in the rightward partition space 27a as shown in FIG. 12. The distal end side of the coil spring 43A is mounted in the prescribed position within the rightward partition space 27a, and the proximal end side of the coil spring 43A is mounted on a spring connecting member 130 integrally fixed on the upward connection member 33R. The upward connection member 33U operates simultaneously with the vertical chain 32a through a sprocket not shown, and a rightward connection member 32R operates simultaneously with the horizontal chain 132a through a sprocket not shown.

According to the present embodiment, when the user releases the fingers from the vertical knob 5a to put the vertical knob 5a in the free state in the pulled state of the coil spring 43A, the rightward connection member 32R and the upward connection member 33U are moved in the reverse direction to the UP direction by the pullback force amount which is the biasing force of the coil spring 43A.

And the vertical chain 32a connected to the upward connection member 33U moves in the DOWN direction. Thus, as with the above-mentioned embodiment, the vertical sprocket 31a having the vertical chain 32a wound around it is turned in the downward bending direction which is the reverse direction to the upward bending direction so that the vertical knob 5a is put in the state of being turned in the downward bending direction. Accordingly, the bending portion 2b having been in the bending state as indicated in full line in FIG. 1 changes toward the approximately straight state.

Thus, it is possible to obtain the same workings and advantages as those of the above-mentioned embodiment.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope including a bending portion in an insertion portion, comprising:
   first and second pulling members mounted on the bending portion;
   a bending operation knob for generating a driving force for pulling the pulling members in conjunction with a turning operation and bending the bending portion between an approximately straight state and a bending state;
   a driving force transfer mechanism for transferring the driving force generated in conjunction with the turning operation of the bending operation knob to one of the first and second pulling members mounted on the bending portion;
   a biasing mechanism including:
      a coil spring which is a push spring provided approximately in parallel with a moving direction of the pulling members;
      a fixing member for integrally fixing a side of one end face of the coil spring on an operation portion;
      a sliding member placed separately from and opposite an other end face of the coil spring; and
      an arm portion forming member for integrally connecting the sliding member to a predetermined position of a connecting member connected to the driving force transfer mechanism which is moved in conjunction with a turning operation of the bending operation knob, when the bending portion is bent by turning the bending operation knob and pulling the first pulling member, the biasing mechanism being adapted for providing a biasing force for turning the bending operation knob in a reverse direction to a direction of the turning operation by the sliding member being moved with movement of the driving force transfer mechanism and contacting the other end face of the coil spring, in a state where the bending portion is bent by turning the bending operation knob and pulling the first pulling member of the first and second pulling members; and
   a connection member axially connecting the driving force transfer mechanism to the one of the first pulling member and the second pulling member, wherein the connection member comprises mounting holes for receiving the arm portion forming member;
   wherein the push spring imparts a compressive force to the sliding member for biasing the bending portion from the bending state to the approximately straight state.

2. The endoscope according to claim 1, wherein:
in a state where the bending operation knob is turned,
the biasing mechanism provides the driving force transfer mechanism with a biasing force for biasing the bending portion bent by the turning operation of the bending operation knob in a direction of the approximately straight state.

3. An endoscope including a bending portion in an insertion portion, comprising:
first and second pulling members mounted on the bending portion;
a driving force transfer mechanism for transferring a rotary driving force generated by a bending operation knob to a corresponding pulling member and pulling one of the first and second pulling members mounted on the bending portion so as to change the bending portion between an approximately straight state and a bending state; and
a biasing mechanism including:
a coil spring which is a push spring provided approximately in parallel with a moving direction of the pulling members;
a fixing member for integrally fixing one end side of the coil spring on an operation portion;
a sliding member placed separately from and opposite an other end face of the coil spring;
an arm portion forming member for integrally connecting the sliding member to a predetermined position of a connecting member connected to the driving force transfer mechanism which is moved in conjunction with a turning operation of the bending operation knob, when the bending portion is bent by turning the bending operation knob and pulling the first pulling member, the biasing mechanism being adapted for providing a biasing force for biasing the bending portion bent by a bending operation of the bending operation knob in an approximately straight direction to the driving force transfer mechanism for transferring the rotary driving force of the bending operation knob operated on bending the bending portion in one direction corresponding to one of the first and second pulling members; and
a connection member axially connecting the driving force transfer mechanism to the one of the first pulling member and the second pulling member, wherein the connection member comprises mounting holes for receiving the arm portion forming member;
wherein the push spring imparts a compressive force to the sliding member for biasing the bending portion from the bending state to the approximately straight state.

4. The endoscope according to claim 1, wherein the coil spring is placed in a space portion formed between the first and second pulling members which are mutually opposed, the first pulling member having a proximal end portion connected to one end of the driving force transfer mechanism and the second pulling member having a proximal end portion connected to another end of the driving force transfer mechanism.

5. The endoscope according to claim 3, wherein the coil spring is placed in a space portion formed between the first and second pulling members which are mutually opposed, the first pulling member having a proximal end portion connected to one end of the driving force transfer mechanism and the second pulling member having a proximal end portion connected to another end of the driving force transfer mechanism.

6. An endoscope including a bending portion in an insertion portion, comprising:
first and second pulling members mounted on the bending portion;
bending operation knob for generating a driving force for pulling the pulling members in conjunction with a turning operation and bending the bending portion between an approximately straight state and a bending state;
a driving force transfer mechanism for transferring the driving force generated in conjunction with the turning operation of the bending operation knob to one of the first and second pulling members mounted on the bending portion: and
a biasing mechanism including:
a coil spring which is a pull spring provided approximately in parallel with a moving direction of the pulling members;
a fixing member for integrally fixing one end side of the coil spring on an operation portion;
a sliding member connected to an end face of the coil spring; and
an arm portion forming member for integrally connecting the sliding member to a predetermined position of a connecting member connected to the driving force transfer mechanism which is moved in conjunction with a turning operation of the bending operation knob, the biasing mechanism being adapted for providing a biasing force for turning the bending operation knob in a reverse direction to a direction of the turning operation by the sliding member being moved with movement of the driving force transfer mechanism and contacting an other end face of the coil spring, in a state where the bending portion is bent by turning the bending operation knob; and
a connection member axially connecting the driving force transfer mechanism to the one of the first pulling member and the second pulling member, wherein the connection member comprises mounting holes for receiving the arm portion forming member;
wherein the pull spring imparts a tensile force to the sliding member for biasing the bending portion from the bending state to the approximately straight state.

7. An endoscope including a bending portion in an insertion portion, comprising:
first and second pulling members mounted on the bending portion;
a driving force transfer mechanism for transferring a rotary driving force generated by bending operation knob to a corresponding pulling member and pulling one of the first and second pulling members mounted on the bending portion so as to change the bending portion between an approximately straight state and a bending state;
a biasing mechanism including:
a coil spring which is a pull spring provided approximately in parallel with a moving direction of the pulling members;
a fixing member for integrally fixing one end side of the coil spring on an operation portion;
a sliding member placed separately from and opposite an end face of the coil spring; and
an arm portion forming member for integrally connecting the sliding member to a predetermined position of a connecting member connected to the driving force transfer mechanism which is moved in conjunction with a turning operation of the bending operation knob, when the bending portion is bent by turning the bending operation knob and pulling the first pulling member, the biasing mechanism being adapted for providing a biasing force for biasing the bending portion bent by a bending operation of the bending operation knob in an approximately straight direction to the driving force transfer mechanism for transferring the rotary driving force of the bending operation knob operated on bending the bending portion in one direction corresponding to one of the first and second pulling members; and a connection member axially connecting the driving force transfer mechanism to the one of the first pulling member and the second pulling member, wherein the connection member comprises mounting holes for receiving the arm portion forming member;

wherein the pull spring imparts a tensile force to the sliding member for biasing the bending portion from the bending state to the approximately straight state.

8. The endoscope according to claim 6, wherein the coil spring is placed in a space portion formed between the first and second pulling members which are mutually opposed, the first pulling member having a proximal end portion connected to one end of the driving force transfer mechanism and the second pulling member having a proximal end portion connected to another end of the driving force transfer mechanism.

9. The endoscope according to claim 7, wherein the coil spring is placed in a space portion formed between the first and second pulling members which are mutually opposed, the first pulling member having a proximal end portion connected to one end of the driving force transfer mechanism and the second pulling member having a proximal end portion connected to the another end of the driving force transfer mechanism.

10. The endoscope according to claim 8, wherein the pulling member is inserted into a space in which the driving force transfer mechanism is arranged.

11. The endoscope according to claim 9, wherein the pulling member is inserted into a space in which the driving force transfer mechanism is arranged.

12. The endoscope according to claim 1, wherein the driving force transfer mechanism is a chain.

13. The endoscope according to claim 3, wherein the driving force transfer mechanism is a chain.

14. The endoscope according to claim 6, wherein the driving force transfer mechanism is a chain.

15. The endoscope according to claim 7, wherein the driving force transfer mechanism is a chain.

* * * * *